(12) United States Patent
Tyvoll et al.

(10) Patent No.: US 7,112,433 B2
(45) Date of Patent: *Sep. 26, 2006

(54) ELECTRICAL ANALYSIS OF BIOLOGICAL MEMBRANES

(75) Inventors: David Tyvoll, La Jolla, CA (US); Winthrop D. Childers, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 426 days.

This patent is subject to a terminal disclaimer.

(21) Appl. No.: 10/423,166

(22) Filed: Apr. 24, 2003

(65) Prior Publication Data

US 2004/0214312 A1    Oct. 28, 2004

(51) Int. Cl.
C12M 1/34    (2006.01)

(52) U.S. Cl. .............................. 435/288.4; 435/288.5; 204/403.01; 204/403.03

(58) Field of Classification Search .................... None
See application file for complete search history.

(56) References Cited

U.S. PATENT DOCUMENTS

| | | |
|---|---|---|
| 6,315,940 B1 | 11/2001 | Nisch et al. |
| 6,368,851 B1 | 4/2002 | Baumann et al. |
| 6,379,916 B1 | 4/2002 | Meyer |
| 6,488,829 B1 | 12/2002 | Schroeder et al. |
| 6,699,697 B1 * | 3/2004 | Klemic et al. ............ 435/173.4 |
| 6,770,441 B1 * | 8/2004 | Dickinson et al. ............. 435/6 |
| 6,896,780 B1 * | 5/2005 | Yang et al. .................. 204/408 |
| 2002/0064841 A1 | 5/2002 | Klemic et al. |
| 2003/0005771 A1 | 1/2003 | Degertekin |

FOREIGN PATENT DOCUMENTS

| | | |
|---|---|---|
| EP | 1352952 | 10/2003 |
| WO | WO0108800 | 2/2001 |
| WO | WO0159447 | 8/2001 |
| WO | WO 02/077259 | 10/2002 |

OTHER PUBLICATIONS

"Effect of Internal Fluoride and Phosphate on Membrane Currents During Intacellular Dialysis of Nerve Cells", Kostyuk et al., Nature, vol. 257, Oct. 23, 1975.
"Patch Clamp Techniques: An Overview", Cahalan et al., Methods in Enzymology, vol. 207, pp. 3-15, 1992.
"High Quality Patch Clamp Recordings on a Chip", AVIVA Biosciences Corporation, Feb. 2002.
"Patch Clamping Approaches" and "CytoPatch Chip", Cytocentrics, pp. 2-3, Oct. 2002.

* cited by examiner

*Primary Examiner*—David Redding

(57) ABSTRACT

A biochip device for electrical analysis of biological membranes. The device may include a substrate assembly defining an array of apertures and including thin-film devices configured to sense an electrical property of biological membranes that seal the apertures. The device also may include an electrical interface coupled electrically to the thin-film devices and configured to electrically couple the thin-film devices to a control apparatus. The electrical interface may define a plurality of interface elements, and the apertures may be in excess over the interface elements.

18 Claims, 6 Drawing Sheets

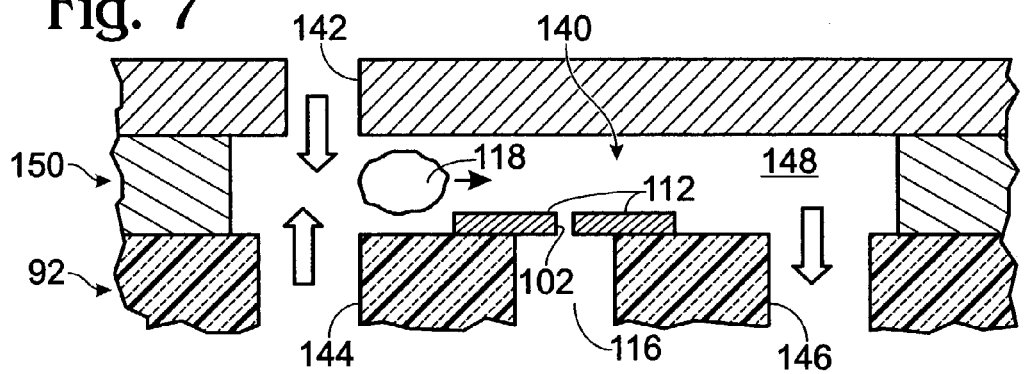
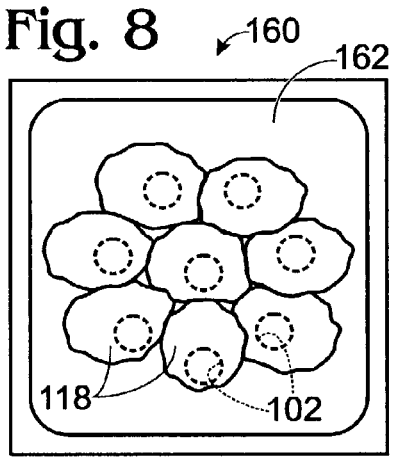
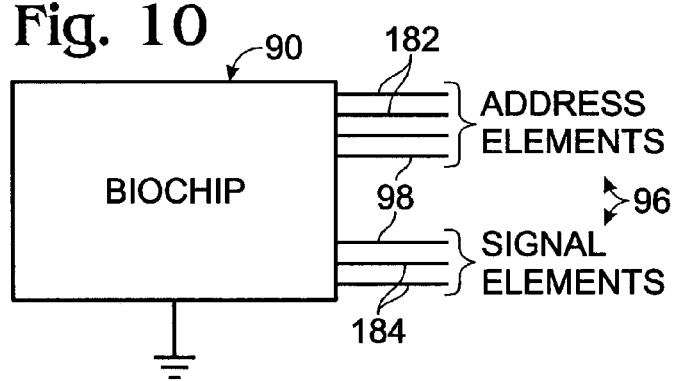
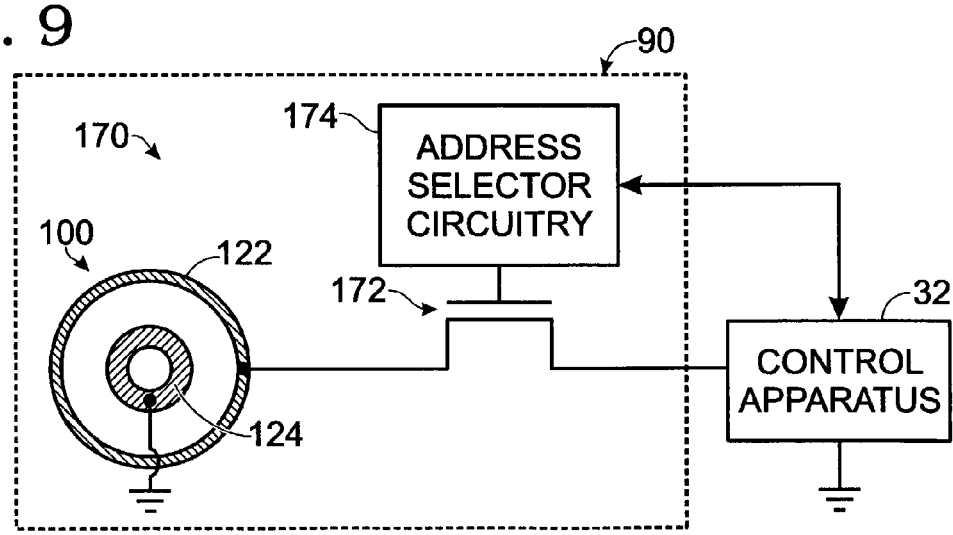

ELECTRICAL ANALYSIS OF BIOLOGICAL MEMBRANES

BACKGROUND

Analysis of cells by patch clamping is a powerful electrophysiological recording technique. Patch clamping is used to study electrical properties of cell membranes, particularly activity and regulation of ion channels included in the membranes. This technique has gained popularity as a measurement tool because it is one of the most direct and meaningful ways to study how the activity of ion channel proteins is modulated by physiological factors in general, and pharmaceutical compounds in particular.

Patch clamping was developed as a procedure performed manually. In traditional patch clamping, a glass pipet of small diameter is placed against the membrane of a cell. Application of a vacuum to fluid in the interior of the pipet pulls the membrane against the end of the pipet, creating a tight, resistive seal between the perimeter of the pipet end and a "patch" on the membrane. This seal, often termed a gigaseal because of its gigohm or near-gigohm resistance, directs electrical current along a path from the bore of the pipet through the patch and/or the whole cell. When the patch is permeabilized selectively, the electrical properties of the remainder of the cell membrane, other than the patch, may be measured in a whole-cell analysis. Alternatively, the remainder the cell membrane may be removed, leaving only the patch to be analyzed.

In either case, a current or voltage applied across the cell or patch membrane may be measured. For example, a "stimulation" voltage may be applied between 1) an "external" electrolytic fluid that holds the cell (or patch) and 2) an "internal" electrolytic fluid in the interior of the pipet. Such a stimulation voltage produces a corresponding response in ion flow (and thus the electrical current) through the whole cell membrane or membrane patch. The impedance of the membrane determines the magnitude of the current. Ligand- and/or voltage-induced changes in ion channel activity thus produce corresponding changes in the impedance of the membrane and in the magnitude of the current. In a typical approach, the voltage (or current) may be fixed or "clamped" during analysis, while the resultant current (or voltage) is measured, thereby producing a voltage-(or current) clamped analysis.

Despite the sensitivity of the patch-clamp method, the manual approach with a pipet may not be suitable for analysis of libraries of compounds, such as in high-throughput drug screens. In particular, with the manual approach, cells are analyzed one at a time. Accordingly, testing the effects of chemical compounds may be too slow to screen large numbers of candidate compounds.

Efforts to improve the speed of patch-clamp analysis have focused on analyzing more than one cell at once. For example, the single pipet may be replaced with an array of apertures defined by a planar material. With such a "planar patch-clamp" device, cells may be disposed at each of the apertures and electrically monitored with circuits specific for each aperture.

Despite their potential for increased throughput, these planar patch-clamp devices may be inadequate for a number of reasons. For example, some patch-clamp devices use movable electrodes that are not dedicated to individual apertures. Such devices may limit the number of apertures that can be excited and monitored in parallel and increase the incidence of mechanical malfunction with moving parts. Other patch-clamp devices may include dedicated monitoring circuits but lack integration of their circuitry, for example, having a separate sensor circuit for each aperture. Such separate circuits place a practical limit on the density of apertures that may be included, based on the size and complexity of the resulting electrical interface. Accordingly, this aperture limit places a corresponding limit on the number of cells/compounds/conditions that may be analyzed in an experiment. Furthermore, such insufficiently integrated devices may not allow the conditions at individual apertures to be monitored and modified automatically and selectively.

SUMMARY

A biochip device is provided for electrical analysis of biological membranes. The device may include a substrate assembly defining an array of apertures and having thin-film devices configured to sense an electrical property of biological membranes that seal the apertures. The device also may include an electrical interface coupled electrically to the thin-film devices and configured to electrically couple the thin-film devices to a control apparatus. The electrical interface may define a plurality of interface elements, and the apertures may be in excess over the interface elements.

BRIEF DESCRIPTION OF THE DRAWINGS

FIG. 7 is a sectional view of an alternative embodiment of an examination site that may be included in a biochip device for electrical analysis of cells.

FIG. 8 is a plan view of an embodiment of a set of examination sites for electrical analysis of a group of cells disposed in a shared fluid compartment.

FIG. 9 is a schematic view of an embodiment of a circuit that electrically couples an examination site of a biochip to a control apparatus.

FIG. 10 is a schematic view of an embodiment of a biochip device and its electrical interface for addressing examination sites of the device.

DETAILED DESCRIPTION

Figure 1:
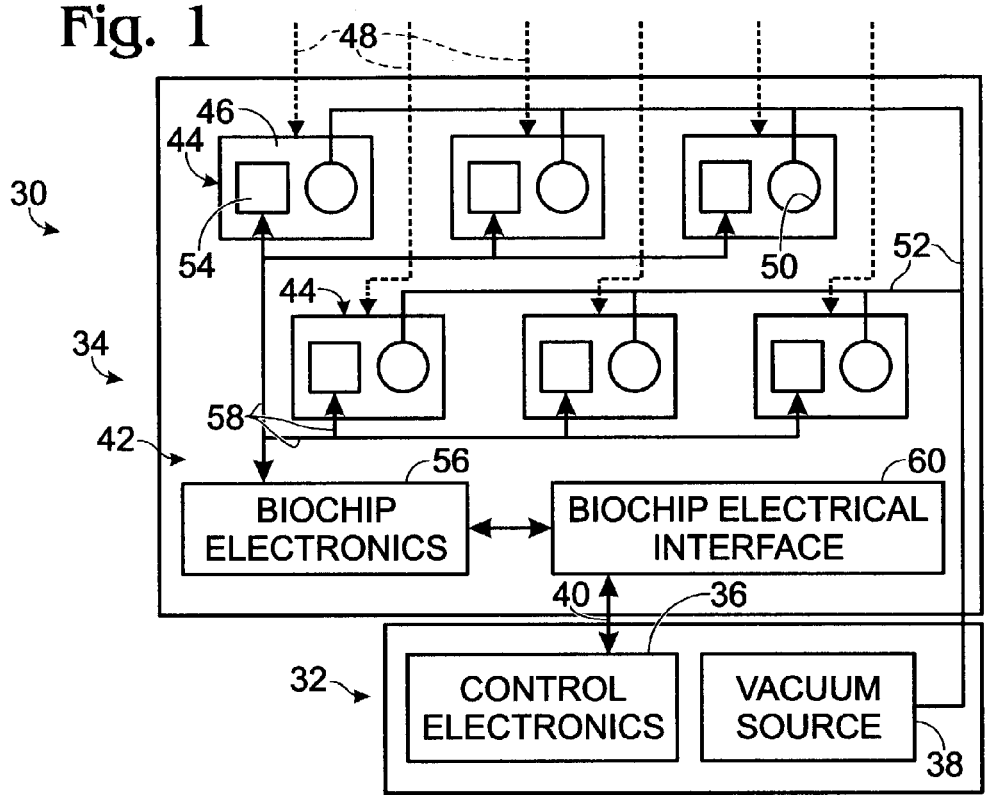
FIG. 1 is a schematic view of an embodiment of a test system for electrical analysis of cells at an array of examination sites defined by a biochip device of the system.

A test system is provided for electrical analysis of biological membranes. The system may include a biochip device and a control apparatus that powers and electronically controls the biochip device. The biological membranes may be provided by whole cells, fragments of cells, and/or reconstituted membranes that include a membrane component(s) from cells.

The biochip device may include a substrate assembly having an array of examination sites. As used herein, an examination site is a region of the device configured to examine one or more electrical properties of a biological membrane and/or cell disposed at the examination site. Each examination site may include an aperture configured to be covered (or sealed) by a biological membrane. Each examination site also may include one or more thin-film devices for monitoring conditions, modifying conditions, and/or performing measurements at the examination site. Furthermore, each examination site may include or define a compartment for holding fluid and the biological membrane/cell. The biochip device also may include an electrical interface having a plurality of discrete interface elements or inputs configured to electrically couple the thin-film devices to the control apparatus. Electronic circuitry of the biochip device that couples to the thin-film devices may be highly integrated using solid-state switching devices so that the number of examination sites and apertures exceeds the number of interface elements at the electrical interface.

The test system and biochip device described herein may be used to perform methods for electrical analysis of cells and biological membranes. Thin-film devices at selected subsets or all of the examination sites may be electrically energized in parallel and/or in series, as appropriate, based on the stage of the analysis, measured results from the examination site, and/or the like. For example, examination sites may be selectively energized automatically based on comparison of a measured electrical property from each site with a threshold value. This approach may be used, for example, to restrict additional operations to examination sites at which membranes effectively seal the apertures or to reposition cells over apertures that are not effectively sealed, among others.

Each examination site may include any suitable number of individually addressable thin-film devices. Such thin-film devices may include one or more electrodes for providing an electrical stimulus to the membrane disposed at the aperture and for monitoring a resultant electrical response from the membrane. In some embodiments, the same or different electrodes may be used as an alignment electrode, that is, an electrode configured to produce an electric field that moves a cell or membrane toward the aperture of the examination site. The thin-film devices also may include an ultrasonic transducer, a heater, a temperature sensor, an orifice bubbler, and/or an optoelectronic device, among others. Accordingly, integrated electronic circuitry of the biochip device may be used to activate the thin-film devices together or in an orchestrated sequence using electronic switching devices according to the needs of the analysis and measured configuration at the examination site. Therefore, the biochip device and test system described herein, may be used to analyze a larger number of biological samples, under a greater number of conditions, with increased automation and control.

FIG. 1 shows a schematic view of an embodiment of a test system 30 for electrical analysis of biological membranes/cells. System 30 may include a control apparatus 32 and a biochip device 34.

The control apparatus may be any electronic device for directing operation of test system 30, generally in response to user inputs. The control apparatus may include a power supply (not shown), control electronics 36, and a vacuum source 38, among others. The power supply may provide power to biochip device 34 and to accessory mechanisms included in the control apparatus or under its control. Control electronics 36 may include any suitable electronic circuitry configured to direct operation of biochip device 34 by exchanging signals with the biochip device, shown at 40. The control electronics may include a digital processor, memory, software instructions, output devices (such as a printer, monitor, etc.) and electronic sensors, among others. The control electronics may be controlled by a user at a user interface of the control apparatus (such as a keyboard, keypad, mouse, etc.). Vacuum source 38 may be included in control apparatus 32 or may be provided by a separate apparatus. In either case, vacuum source 38 may be used to supply a negative pressure to the biochip device, as needed, for example, to pull biological membranes against apertures of the biochip device.

Biochip device 34 may be configured as a separate device that interfaces with the control apparatus. As used herein, a biochip device is any device that includes an array of test or examination sites arranged on a substrate. The biochip device may be a single-use, disposable device or may be reusable. The biochip device may provide a substrate assembly 42 at least partially defining an array of examination sites 44 for measuring electrical properties of biological membranes. Each examination site is configured to measure electrical properties of a distinct biological membrane. The biochip device may have at least about one hundred (or at least about one thousand) examination sites and the examination sites may have a density at least about one (or at least about ten) per square millimeter. Each examination site 44 may include a fluid compartment 46 for holding an electrolytic fluid in which one or more biological membranes may be disposed. Fluid compartments 46 may be individually and/or collectively addressed by fluid inputs 48, which may be externally or internally accessible openings, fluid conduits, pipets, etc. Each examination site 44 also may include an aperture 50 (or a plurality of apertures). Apertures also may be described as orifices, and in some embodiments, may act as drains through which fluid flows. Each aperture may be in fluid connection with vacuum source 38 using vacuum conduits 52, so that a negative pressure may be applied to the aperture. In this case, the aperture may serve both to attract a cell via negative pressure as well as to seal and electrically record the cell. Alternatively, the aperture may function solely to seal and electrically record the cell or membrane, and negative pressure may still be applied to the cell by a separate, concentric channel surrounding the aperture. Site 44 also may include thin-film devices 54 that are selectively addressed to create electric or magnetic fields, provide ultrasonic energy, generate heat, provide light, and/or act as corresponding energy sensors.

Substrate assembly 42 may include biochip electronics 56, which provide selectively addressable, electrically conductive pathways 58 to thin-film devices 54. Biochip electronics 56 may be formed by any suitable fabrication process and may have any suitable level of integration. Accordingly, biochip electronics 56 may include digital-analog and analog-digital converters and/or switching networks for selecting, energizing, and/or monitoring the thin-film devices, as described further below.

Biochip electronics 56 and thin-film devices 54 may be electrically coupled to control apparatus 32, shown at 40, through biochip electrical interface 60. Electrical interface 60 may be attached to substrate assembly 42, for example, on an external surface thereof, to provide conductive or inductive coupling to electronics 36 of the control apparatus. Electrical interface 60 may provide a set of separate interface elements, which are described more fully below.

Figure 2:
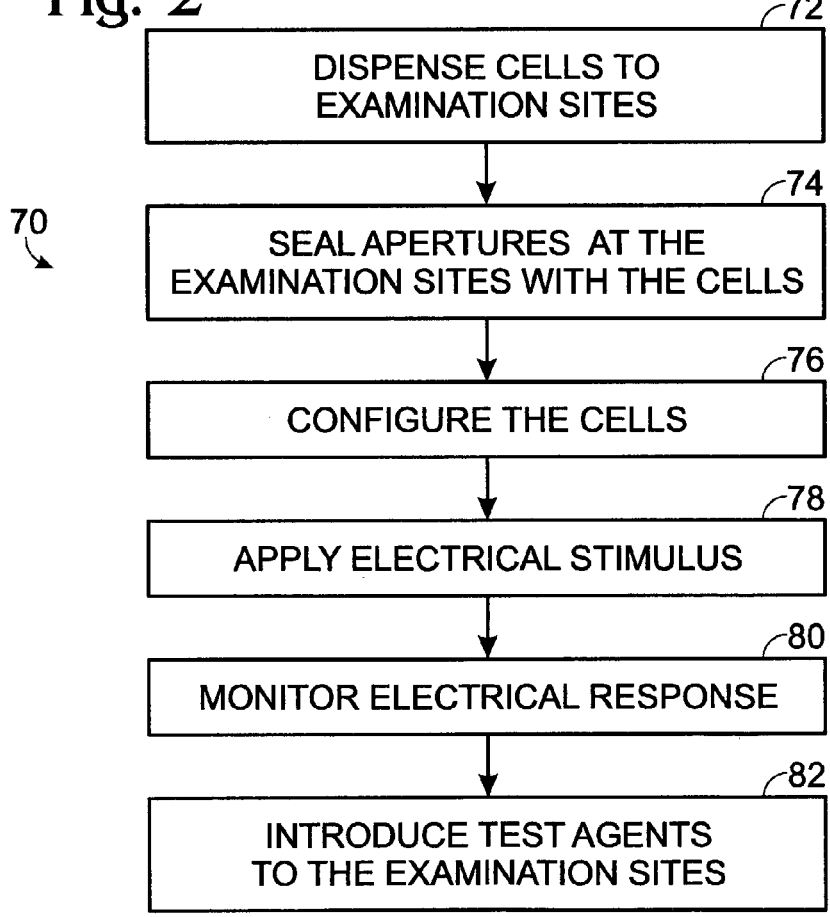
FIG. 2 is a flowchart showing an embodiment of a method for electrical analysis of cells using the system of FIG. 1.

FIG. 2 shows an embodiment of a method 70 for electrical analysis of cells using test system 30 of FIG. 1.

In method 70, cells are dispensed to examination sites, as shown at 72. The cells may be disposed at fluid compartments 46 of sites 44 by individually dispensing portions of a cell suspension, for example, with an automated fluid delivery device, to each site, so that one or more cells is deposited at the site. Alternatively, fluid compartments 46 may be addressed together, for example, by adding a cell suspension in a volume large enough to place the fluid compartments in fluid communication or by using conduits that interconnect the fluid compartments. In some embodiments, fluid (carrying cells) is introduced in general alignment with each aperture to promote gravity mediated movement of a cell toward the aperture as the cell settles out of suspension.

In other embodiments, any suitable biological membrane may be dispensed to, or formed at, the examination sites. Biological membranes generally include any lipid bilayer and may be biological membranes, carrying a biomolecule (s) that promotes or regulates ion flow through the bilayer. The lipid bilayer may be provided by a cell, a virus, an organelle, a vesicle, and/or the like, and thus may be naturally occurring or produced artificially. The biomolecule may be produced by cell, or may be an artificial derivative or mimic thereof. Exemplary molecules that may promote or regulate ion flow include integral or peripheral membrane proteins, such as ion channels or transporters, or may be channel-forming synthetic compounds, among others.

Apertures of the examination sites then may be sealed with a membrane, as shown at 74. The membrane generally corresponds to a portion of the cell's original membrane. As used herein, an aperture sealed with a membrane has a greater resistance than an unsealed aperture, typically substantially greater. In some embodiments, sealing may provide a kilohm, a megohm, or a gigohm resistance to current flow through the aperture. A subset of the apertures may not be sealed. Sealing may include moving the cells to a position adjacent the apertures and then pulling the cells into sealed contact with the apertures. Moving may be promoted by applying an electrical field that electrically polarizes the cell. Alternatively, or in addition, moving may be promoted by ultrasonic agitation, fluid flow, induced or random cell migration, and/or a pressure on fluid in which the cells are included. Similarly, pulling the cells into sealed contact may be promoted by a vacuum, positive pressure, fluid flow, molecular interactions between the substrate assembly and the cells, an electric field, and/or the like.

After cells have sealed at least some of the apertures, the cells may be analyzed in the cell-attached mode (CA mode), in which a whole cell may be disposed in sealed contact with an aperture. Optionally, the cells may be further configured from the cell-attached configuration before analysis, as shown at 76. Configuring the cells may include spatially restricted removal or perforation of the cell membranes. The removal or perforation may be performed selectively within the membrane patch bounded by the aperture or on the remainder of the cell membrane (other than the patch) extending away from the aperture. Suitable methods of removal or perforation may include directing an agent or treatment to the membrane patch from the aperture and/or from outside the cell in the fluid compartment. Such agents or treatments may include a voltage pulse, local heating, a detergent, a pressure pulse, a pore-forming material (such as nystatin or amphotericin), and/or the like. Accordingly, after configuration of the cells, they may be used for analysis of whole cells (WC mode), inside-out membrane patches (IO mode), or outside out patches (OO mode).

An electrical stimulus then may be applied, as shown at 78. The electrical stimulus may correspond to a clamped-voltage, a clamped-current, and/or a varying voltage or current of any suitable pattern, frequency, amplitude, etc. The electrical stimulus may be an electric field or electrical signal that preferably extends or travels across a cell membrane or membrane patch that seals the aperture. The electrical stimulus may be provided between any suitable electrodes, although preferably thin-film electrodes formed by depositing and patterning conductive thin films on a substrate are used.

An electrical response resulting from the electrical stimulus then may be monitored (sensed/measured), as shown at 80. The electrical response may be a current, voltage, impedance (or resistance), etc., and may be monitored as a function of time, at a single time point, as a time-averaged value, etc. The electronic circuitry of the biochip device and/or the control apparatus may include suitable amplifiers to amplify the response.

Test agents then may be introduced to the examination sites, as shown at 82, for example, by addition of the agents to the fluid compartments adjacent the apertures. Introduction of the test agents may be contingent upon the measured electrical response. In addition, introduction of the test agents may be automated, for example, controlled by the electronics of the biochip and/or control apparatus. Suitable test agents may be chemical, biological, and/or physical. Chemical test agents, such as drug candidates, may include compounds, polymers, mixtures, solutions, etc. Physical test agents may include heat, light (electromagnetic radiation), particles, magnetic fields, electric fields/current, sound, and/or the like. Biological test agents may include cells, viruses, organelles, or extracts or components thereof.

FIGS. 3–6 show an embodiment of a biochip device 90 that may be included in the test system of FIG. 1. Biochip device 90 corresponds generally to device 34 of FIG. 1 and may include any of the components or features described above for device 34, such as a substrate assembly 92 having the general arrangement of substrate assembly 42 in FIG. 1.

Figure 3:
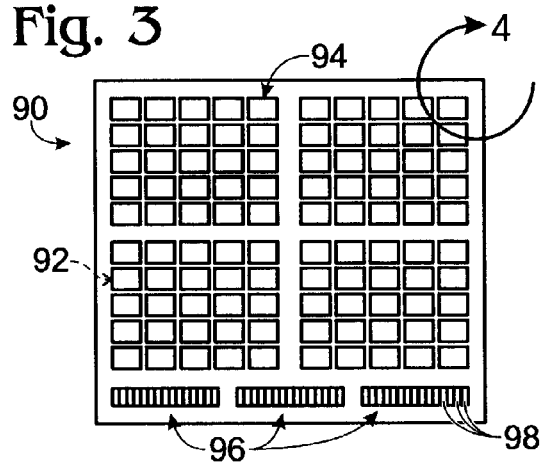
FIG. 3 is a plan view of an embodiment of a biochip device that may be included in the system of FIG. 1.

FIG. 3 shows biochip device 90 with an array of examination groups 94. In an exemplary embodiment, device 90 may have one hundred examination groups, although any suitable number of such groups may be included in the device. Each examination group 94 may be disposed adjacent and/or included in a distinct region of substrate assembly 92 and thus may provide fluidic and/or electronic organization within the biochip device. In some embodiments, each examination group may define a signal group, as described more fully in relation to FIGS. 9–11.

Biochip device 90 also may include an electrical interface 96, corresponding functionally to electrical interface 60 of FIG. 1. Electrical interface 96 may provide a plurality of discrete and separate interface elements 98 through which electronic circuitry of device 90 may be electrically coupled to a control apparatus. Electrical interface elements also may be described as inputs through which electrical signals (analog or digital) are passed to the biochip device to select switching devices and/or thin-film devices. Each interface element 98 may be an electrically conductive contact site or may provide inductive coupling, among others. Accordingly, in some embodiments, interface elements 98 may be disposed at an external surface of device 90. The interface elements may be formed of any conductive material, such as a metal or metal alloy (platinum, gold, copper, aluminum, etc.).

Interfacing to the biochip device may be accomplished via a flexible or PC board type interconnect circuit to provide the interface elements. The interconnect circuit may be coupled to the biochip device via a suitable coupling method, such as wire bonds, solder bonds, or TAB bonding, among others. The interconnect circuit may include "make/break" contacts for coupling to the rest of the test system. The "make/break" contacts may be a contact pad array, a pin connector, or the like.

In some embodiments, the biochip device may be part of a "plug-in module" that includes the biochip device plus an interfacing portion(s) that may include a plastic housing(s), mechanical latching and datum features, interconnect circuitry, and fluidic couplers.

Figure 4:
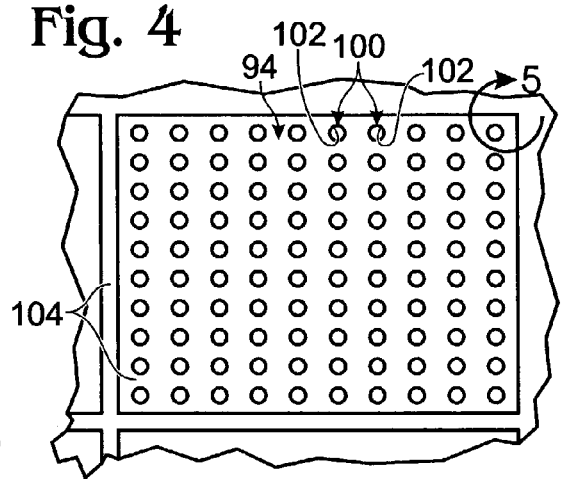
FIG. 4 is a magnified view of an examination group of the biochip device of FIG. 3, indicated at "4" in FIG. 3.

FIG. 4 shows a magnified view of an examination group 94 of biochip device 90. Examination group 94 may include an array of examination sites 100 each having an aperture 102. In an exemplary embodiment, each examination group may have one hundred examination sites, to provide a total of ten thousand examination sites in the device. This exemplary embodiment may have fluid compartments or wells of about 100 micrometers in diameter, a center-to-center spacing between wells of about 200 micrometers, and an overall dimension of about two centimeters on a side. However, other embodiments may have any suitable dimensions. Apertures 102 may be sized to have a diameter that is less than the diameter of a cell, particularly a eukaryotic cell. In some embodiments, the apertures may be about 0.05 to 10 micrometers or about 0.1 to 5 micrometers in diameter. In an exemplary embodiment, the apertures have a diameter of about 2 to 3 microns. In some embodiments, due to the use of electronic switching devices in the biochip device, the total number of apertures and examination sites may exceed the number of interface elements in the electrical interface, or may exceed the number of interface elements by at least about ten-fold. The use of switching devices to enable such integration and addressability is described further below. Examination group 94 also may include a fluid barrier 104. The fluid barrier may surround each examination group and/or may help define and separate individual examination sites. The fluid barrier may be configured to allow examination sites 100 to be addressed individually or together with fluid, but separately from examination sites in other examination groups.

Figure 5:
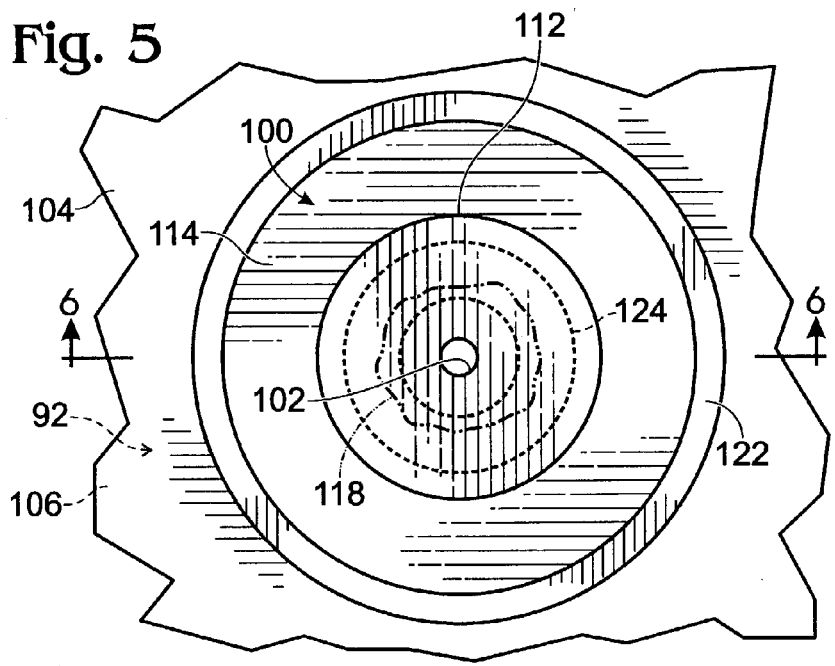
FIG. 5 is a magnified view of an individual examination site from the examination group of FIG. 4, indicated at "5" in FIG. 4.
Figure 6:
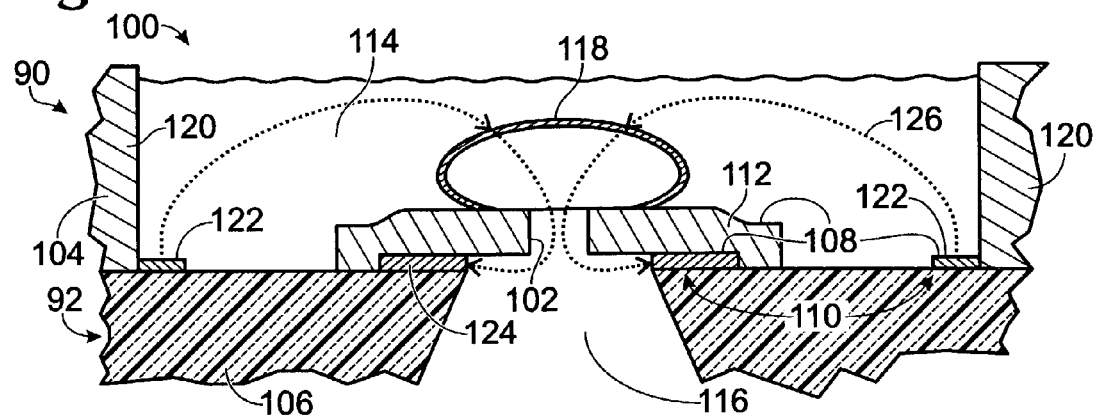
FIG. 6 is a sectional view of the examination site of FIG. 5 with a cell and its membrane positioned for electrical analysis, viewed generally along line 6—6 of FIG. 5.

FIGS. 5 and 6 are magnified plan and sectional views, respectively, of an individual examination site 100 from an examination group 94 of FIG. 4. Examination site 100 may be provided by substrate assembly 92 alone, or in combination with a connected fluid barrier 104.

As used herein, a substrate assembly or base portion is any substrate 106 and associated layers 108 connected to the substrate (see FIG. 6). The substrate assembly may define aperture 102 and may provide electronic circuitry 110 and/or thin-film devices. Substrate 106 may be any base layer and may be formed substantially of a semiconductor and/or an electrical insulator. For example, the substrate may be formed substantially of silicon, glass, alumina, gallium arsenide, plastic, and/or the like. The substrate (and the substrate assembly) may be generally planar, such as a silicon wafer or other sheet-like material.

Associated layers 108 of the substrate assembly may have any suitable shape, thickness, structure, and composition. Layers 108 may include thin films deposited on the substrate in a pattern, or patterned after deposition. The films may define thin-film devices, conductive traces, and/or solid-state switching devices, among others, of electronic circuitry 110. Such thin-film layers may be electrically coupled to electronic devices or components formed in the substrate, for example, by p- and n-doping or to such devices formed adjacent the substrate. Thin-film layers also may include passivation layers or other protective layers disposed over, under, or within the electronic circuitry. Passivation layers near or defining the apertures are especially desirable, since they reduce the capacitance of the substrate and subsequent parasitic currents. Alternatively, or in addition, one or more of layers 108 may define aperture 102. Here, an aperture layer 112 has been connected to substrate 106 and patterned to define aperture 102, although the substrate may provide aperture 102 instead, or in addition. In some embodiments, one or more of layers 108 may define both a fluid barrier and apertures. In these embodiments, the one or more layers may be considered as included partially in each of the substrate assembly and the fluid barrier. Aperture layer 112 may be an electrical insulator, semiconductor, or conductor (for example, an electrode) and may be formed of any patternable material, for example, a negative or positive photoresist (such as SU-8 or PLP), a polyimide, a dry film (such as DuPont Riston), and/or a glass. Methods for patterning aperture layer 112 may include photolithography, laser etching, chemical etching, and/or the like. For example, in the depicted embodiment, aperture layer 112 may be an electrical insulator formed of polyimide. In some embodiments, one or more of layers 108 also may provide fluid feed paths, for example, feeding fluid into channels formed within substrate 106.

Outer and inner fluid compartments, 114 and 116, respectively, may be connected fluidly by aperture 102 on opposing sides of the aperture. These compartments may be defined by substrate assembly 92 and/or fluid barrier 104. The terms "outer" and "inner" are intended to provide relative identifiers, for example, when the fluid compartments are used for whole-cell analysis. One or both may be enclosed or externally accessible. Accordingly, these terms are not intended to define or limit the scope.

Outer compartment 114 may receive and contain one or more cells 118 or other biological membranes, for example, during the steps of method 70 shown in FIG. 2. (To simplify the presentation, FIG. 5 shows a cell 118 in phantom outline over aperture 102, whereas FIG. 6 shows cell 118 in solid outline over the aperture. The position of cell 118 is the same in each of FIGS. 5 and 6.) Outer compartment 114 also may hold a suitable volume of electrolytic fluid in which cell 118 or another biological membrane may be immersed. In some embodiments, the electrolytic fluid during analysis is an aqueous buffer having an ionic composition generally corresponding to a culture medium. Outer compartment 114 may be formed as a well, as shown, so that the compartment is externally accessible, for example, to add/remove/manipulate fluids, cells, test agents, etc. Accordingly, fluid barrier 104 may provide walls 120 of the well and substrate assembly 92 may provide a base or bottom of the well. Alternatively, as described further below, outer compartment 114 may be substantially enclosed, to form a chamber. Fluid compartment 114 may have a volume that is at least several-fold larger than a cell or other biological membrane being analyzed.

Inner compartment 116 may be configured to hold fluid on an opposing side of the aperture from outer compartment 114. This compartment may include some or all of the volume defined by the aperture. The inner compartment may contain a fluid with a composition distinct from that contained in the outer compartment. For example, in whole-cell experiments, the inner compartment may include an electrolytic solution with an ionic composition corresponding generally to the interior of a cell. In addition, the inner compartment may serve as a site for introducing agents or treatments that disrupt the membrane, pull the cell or membrane against the aperture (such as a vacuum), or alter cell physiology or signaling, among others. In some embodiments, the inner compartment may be fluidly isolated from the outer compartment other than through the aperture. Alternatively, some or all of the inner compartments may be included in a shared fluid compartment that communicates fluidly with each of the outer compartments through the apertures. The inner compartment may be defined at least partially by substrate assembly 92, for example, by etching substrate 106. In addition, the inner compartment may be connected to and/or at least partially defined by a fluid manifold configured to deliver fluid to the inner compartment.

Layers 108 may provide thin-film devices to modify and/or sense the properties of fluid and cells/membranes in compartments 114, 116. The thin-film devices may be disposed adjacent outer compartment 114, inner compartment 116, and/or aperture 102. Accordingly, the thin-film devices may be formed adjacent a surface of substrate 106, that is, adjacent outer compartment 114, as shown, and/or adjacent an opposing surface of the substrate. The thin-film devices may be configured to sense or modify fluid/cell/membrane properties in the outer compartment, the inner compartment, and/or between the outer and inner compartments. Such thin-film devices are termed operably disposed at examination site 100. The thin-film devices may include one or more electrical, thermal, pressure, magnetic, and/or optical sensors, among others. Alternatively, or in addition, the thin-film devices may include, but are not limited to, one or more generators of electric fields (electrodes), ultrasound (such as ultrasonic transducers), light (optical transducers), or magnetic fields (magnetic transducers).

Biochip device 90 may be configured to provide electrical stimulation and sense electrical properties between outer and inner compartments 114, 116. In some embodiments, such stimulation and sensing may be provided by electrodes in layers 108 of the substrate assembly. Accordingly, electrodes may be provided as thin-film devices, such as thin films of gold or platinum, among others.

FIGS. 5 and 6 show electrodes that may be used for electrical stimulation and sensing, outer electrode 122 and inner electrode 124. These electrodes may be disposed in outer and inner compartments 114, 116, respectively. Generally, these electrodes act cooperatively as a pair and may be defined or formed at least partially from the same thin-film layer at spaced sites within the layer. As used herein, the same thin-film layer means the film or films deposited during one cycle of thin-film deposition. The electrodes may be configured to provide an electric field 126 extending between the electrodes along a path through the aperture when energized. However, one electrode of the pair may be described as a stimulation and/or sensor electrode that has a partner electrode with which the stimulation or sensor electrode functions. In some embodiments, one of the electrodes may be connected to ground so that the other electrode may be described as a stimulation and/or sensor electrode that stimulates (passes excitation signals) and senses (measures responses to the excitation signals) in relation to a ground electrode.

Inner electrode 124 may have any suitable structure and disposition. For example, inner electrode 124 may be disposed between substrate 106 and aperture layer 112, as shown in FIG. 6. In some embodiments, inner electrode 124 may extend farther toward the aperture axis, so that the inner electrode is at least partially out of contact with the substrate to form an overhang. In some embodiments, inner electrode 124 may define aperture 102, for example, as an overhang as described above. In other embodiments, inner electrode 124 may be disposed on an opposing side of the substrate from outer electrode 122.

One or more of the electrodes may be configured in an annular shape and generally concentric with aperture 102, as shown here. However, each electrode may have any suitable shape and disposition within the outer or inner compartment, respectively. Alternatively, or in addition, rather than thin-film devices included in substrate assembly 92, one or more of the electrodes may be provided as separate devices, for example, by placement of a separate electrode of any type into outer compartment 114 or inner compartment 116.

FIG. 7 shows a sectional view of an alternative embodiment of an examination site 140 from another biochip device for electrical analysis of biological membranes. Examination site 140 may include one or more fluid inlets 142, 144 and one or more fluid outlets 146, to direct fluid flow through outer compartment 148, as indicated by the unfilled arrows. Fluid inlets and outlets may be defined by passages or channels in substrate assembly 92 and/or fluid barrier 150. Fluid inlets and outlets may be used to introduce a cell or another biological membrane into the outer compartment, for washing the cell or membrane, to add test agents, such as drug candidates, for changing the composition of fluid in the outer compartment, etc. A distinct inlet or the same inlet may be used to introduce a cell/biological membrane and a test agent. Valves and/or pumps may be operated selectively to control fluid flow into and out of the outer compartment. In some embodiments, fluid barrier 150 substantially encloses outer compartment 148 to prevent exit of fluid through the barrier. Other features of examination site 140, such as electronic circuitry (and particularly electrodes), have been omitted to simplify the presentation but may be configured as described above.

FIG. 8 is a plan view of an embodiment of a set 160 of examination sites for electrical analysis of a group of cells 118 disposed in a shared fluid compartment 162. Set 160 may include a plurality of apertures 102 in fluid communication with outer compartment 162. Any suitable number of apertures may be used with any suitable spacing. In some embodiments, the apertures may be arranged in a hexagonal distribution with at least one occurrence of six apertures disposed around a central aperture, as shown. Alternatively, the apertures may have a rectilinear, linear, circular, or polygonal arrangement, among others. In some embodiments, the apertures are spaced so that cells 118 are in close proximity or in contact when aligned with apertures 102. Cells in close proximity are spaced to receive paracrine signals from one another, for example, as carried by signaling agents secreted by cells.

Electrodes may be arranged suitably for electrically stimulating and monitoring membranes disposed on apertures 102 of set 160. For example, individual apertures/ examination sites may have separate outer and inner electrodes. Alternatively, the apertures may share an inner electrode, an outer electrode, or an inner and outer electrode.

FIG. 9 shows a schematic view of an embodiment of an addressable circuit 170 that may be included in biochip device 90. As used herein a "circuit" of the biochip device is intended to mean a conductive path or electrically coupled network of conductive paths configured to carry electrical signals. Circuit 170 may be configured to selectively couple an examination site 100 (or a plurality of examination sites) to a control apparatus 32. With selective electrical coupling, an electrode or other thin-film device(s) at the examination site may be addressed independently from other electrodes or other thin-film devices at other examination sites. In this embodiment, circuit 170 includes an outer electrode 122 that may be addressed selectively.

Independently addressing a large number of examination sites, without requiring a correspondingly large number of interface elements and separate circuits, may allow a higher density of examination sites and more flexible addressability of such sites. To achieve such independent addressing, an array of electronic switching devices, such as switching device 172, may be used in the biochip device. In some embodiments, each examination site or each thin-film device may have a corresponding switching device. Exemplary switching devices are solid state, and may include transistors, diodes, or other semiconductive devices. In an exemplary embodiment, switching device 172 may be a field-effect transistor (FET). A gate signal, such as voltage, applied to the FET from control apparatus 32 through address selector circuitry 174 may charge or electrically bias the gate of the FET so that current may flow through circuit 170 between the source and the drain of the FET, to provide a signal connection between test apparatus 32 and outer electrode 122. More generally, any suitable switching devices and coupled thin-film devices may be selected by applying a gate signal to an input of the biochip device.

Control apparatus 32 may address each examination site separately. Accordingly, each site or thin-film device at the site may have a separate address for a given signal connection between control apparatus 32 and the biochip device. Accordingly, one signal connection between the control apparatus and the biochip device may be used to provide electrical coupling to thin-film devices at examination sites independently and serially, or to couple to a set of sites as a group in parallel. In some embodiments, examination sites may be divided into signal groups. Each signal group may have one or more separate signal connections allowing a set of examination sites (from multiple signal groups) to be electrically signaled and monitored in parallel. Such sets of examination sites then may be analyzed in series.

FIG. 10 shows a schematic view of electrical interface 96 of biochip device 90. Electrical interface 96 may include a plurality of interface elements 98 configured to electrically couple biochip device 90 to a control apparatus. In some embodiments, interface elements are of several types: address elements 182, signal elements 184, and one or more ground elements. Each type of element may pass analog or digital electrical signals (as appropriate).

Address elements 182 may be used to select the thin-film devices at particular examination sites that make signal connections to the signal elements. When selected, the thin-film devices may be energized or activated through the signal elements. Address elements may be coupled directly to interface elements. Alternatively, the biochip device may include address selection circuitry (shown at 174 in FIG. 9) for reducing the number of interface elements needed to address (selectively energize) thin-film devices of the chip. Electrical signals, such as voltages, may be applied selectively by the control apparatus to a suitable combination of address elements 182 to allow formation of electrical connections between the signal elements and thin-film devices at examination sites. Accordingly, address selector circuitry of the biochip device may use a relatively small number of address elements to address (selectively energize) a much greater number of thin-film devices. The address selector circuitry may include a network of electronic switching devices or other configurations known in the art. In an exemplary embodiment, 40 address elements may be used to selectively address 10,000 examination sites.

Signal elements 184 may be used to send and receive electrical signals between the control apparatus and electrodes or other thin-film devices. In some embodiments, signal elements may carry signals for electrical stimulation of cells or membranes and for measuring an electrical response resulting from the electrical stimulation. Multiple signal elements may direct independent electrical signals to different thin-film devices, either at the same and/or different examination sites. For example, each signal element may be used to enable electrical analysis of distinct examination sites in parallel, for example, in different signal groups. Alternatively, or in addition, more than one signal element may be used to independently control distinct thin-film devices at one examination site.

Figure 11:
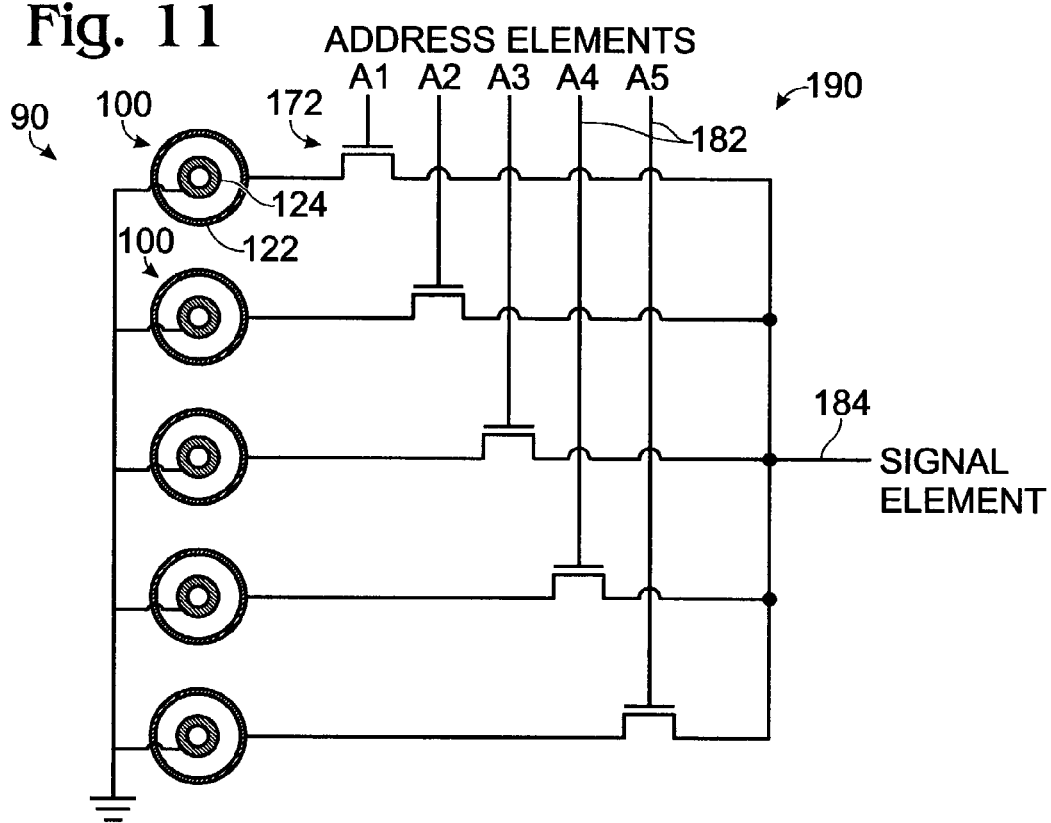
FIG. 11 is a schematic view of a circuit for selectively addressing examination sites included in the system of FIG. 1.

FIG. 11 shows a schematic view of a circuit 190 for addressing different electrodes disposed at a plurality of examination sites 100 in biochip device 90. The electrodes may be addressed together or one at a time. Circuit 190 may include a set of address elements 182 (A1–A5). The address elements may be directly coupled to interface elements or contact pads. Alternatively, A1–A5 may be conductive address leads that connect to address elements using address selector circuitry, for example, to reduce the number of address elements needed to control the address leads. Electrical signals from address elements A1–A5 may select the switching devices 172 that are biased, so that none, only one outer electrode 122, or a selected set of the outer electrodes, may be energized by electrical signals from the signal element 184.

Figure 12:
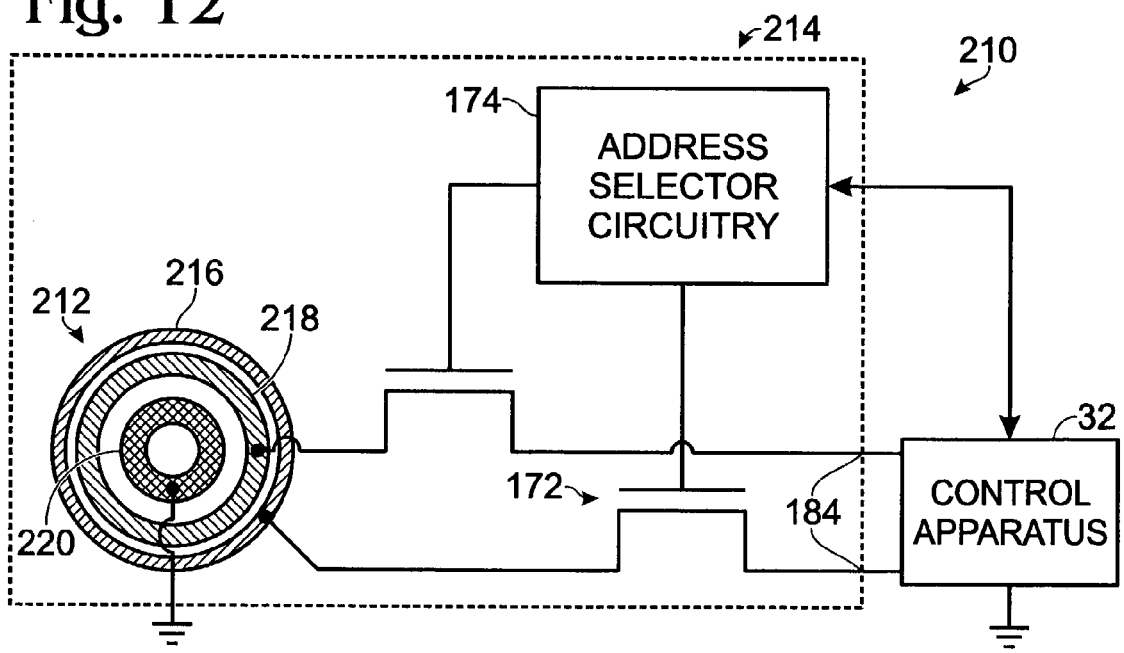
FIG. 12 is a schematic view of a circuit for addressing different electrodes disposed at an examination site included in a biochip device for electrical analysis of cells.

FIG. 12 is a schematic view of a circuit 210 for addressing different electrodes disposed at an examination site 212 of a biochip device 214. Examination site 212 may include at least two outer electrodes 216, 218. Each outer electrode may be connected to a different signal element 184 so that the electrodes are addressable independently by control apparatus 32 through address selector circuitry 174. In addition, each outer electrode may form an electrode pair with inner electrode 220 and may be spaced from the aperture of the examination site. Alternatively, outer electrodes 216, 218 may be used with distinct partner electrodes and/or may be used to form an electric field between the outer electrodes. Outer electrodes 216, 218 may be used to perform different or similar functions, either sequentially or at the same time. For example, one of these outer electrodes may apply an alignment field to move a cell toward alignment with the aperture, while the other may act to stimulate the cell and sense the response after alignment. In some embodiments, first outer electrode 216 may move the cell toward the aperture and second outer electrode 218 may focus the cell more accurately onto the aperture and/or may perform electrical measurements. In other embodiments, the examination site may include three or more independently addressable electrodes.

Figure 13:
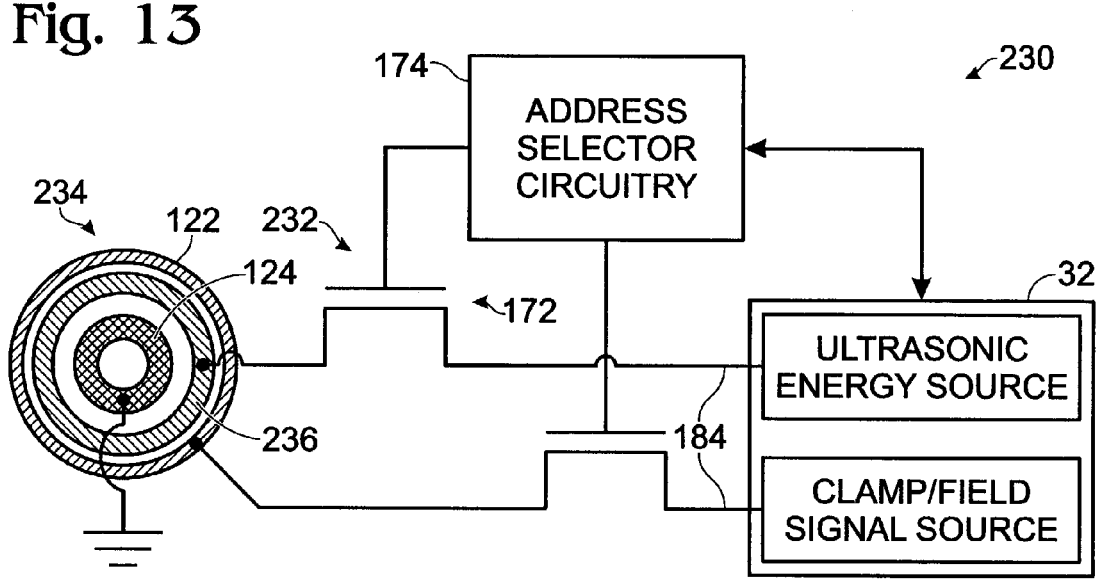
FIG. 13 is a schematic view of a test system having a circuit for addressing distinct thin-film devices disposed at an examination site configured for electrical analysis of cells.

FIG. 13 is a schematic view of a patch-clamp system 230 having a circuit 232 for addressing distinct thin-film devices disposed at an examination site 234 of a biochip device. Control apparatus 32 may provide input signals to control an ultrasonic transducer 236 and sensor electrode 122 using separate signal elements 184. The ultrasonic transducer and sensor electrode may be operated in series or in parallel, as needed. Ultrasonic transducer 236 may be a piezo element disposed adjacent an outer compartment of the examination site. Accordingly, the ultrasonic transducer may be induced to oscillate by applying appropriate electrical signals to the transducer. The ultrasonic transducer may be used, for example, to disaggregate cells/biological membranes, and/or promote their movement. For example, the ultrasonic transducer may be used in conjunction with an electric field formed between electrodes 122, 124 to urge a cell toward the aperture.

More generally, each examination site may include at least one circuit. The at least one circuit may include one, two, three, four, or more thin-film devices. The thin-film devices may include a measurement (sensor) electrode, an alignment electrode, an ultrasonic transducer, a heater, a temperature sensor, etc. Each thin-film device may be coupled to a separate switching device so that the device is independently addressable. Alternatively, any two or more of the thin-film devices may be coupled to the same switching device, so that they are operated in parallel.

Figure 14:
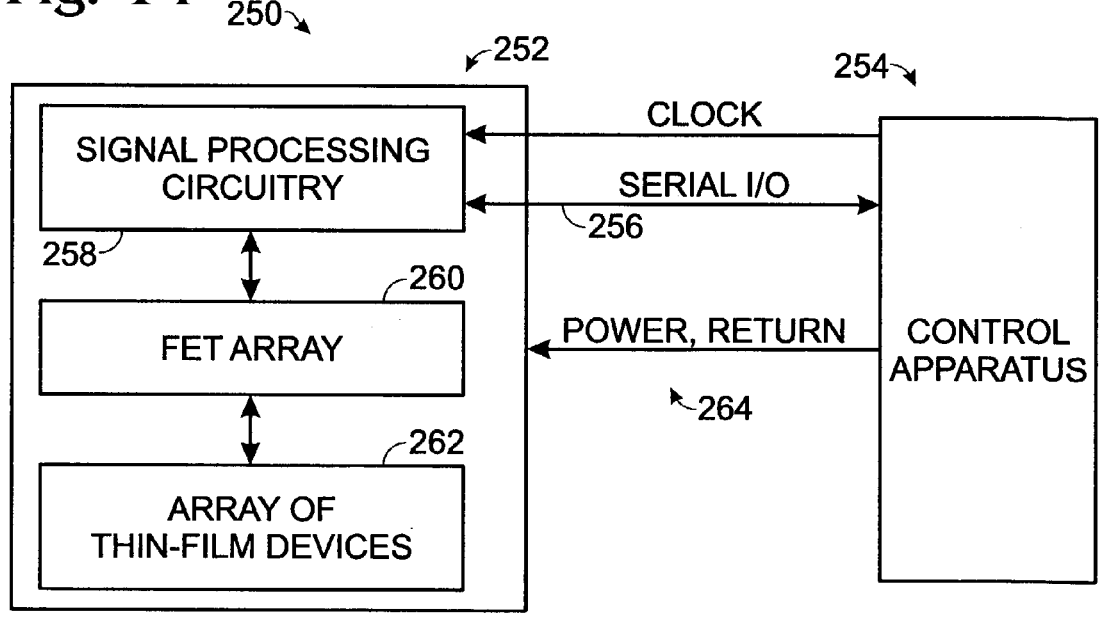
FIG. 14 is a schematic view of an embodiment of a test system for electrical analysis of cells in which a biochip device is coupled to a control apparatus by digital signaling.

FIG. 14 is a schematic view of an embodiment of a patch-clamp system 250 in which a biochip device 252 is coupled to a control apparatus 254 via a serial interface, shown at 256. Electronic circuitry of biochip device 252 may include CMOS-based electronic components and signal processing circuitry 258, such as digital-to-analog (D/A) and analog-to-digital (A/D) converters. Digital words or binary address signals may be passed to biochip device 252 from control apparatus 254. Such words or signals may be converted to analog signals by the biochip device and sent to an array of electronic switching devices, such as FET array 260, and analog signals received from the FET array may be converted to digital words to send to control apparatus 254 for further processing. Accordingly, binary address signals may be used to select switching devices, such as FETS within FET array 260 through the signal processing circuitry. The FETS selected by the signal processing circuitry may provide addressing for thin-film devices at desired examination sites within an array of thin-film devices 262. Accordingly, the binary address signals may select individual thin-film devices or sets of such devices for energization.

Chip interface 264 may include digital I/O lines, a clock line, one or more power lines, and a ground line, among others, for communication between control apparatus 254 and biochip device 252. This interface may be simplified relative to analog interfaces described above. In addition, serial I/O from the control apparatus may be used to perform operations in parallel on the biochip device. Accordingly, there may be fewer constraints on the sequence in which thin-film devices are energized and the extent to which examination sites are analyzed in parallel.

Figure 15:
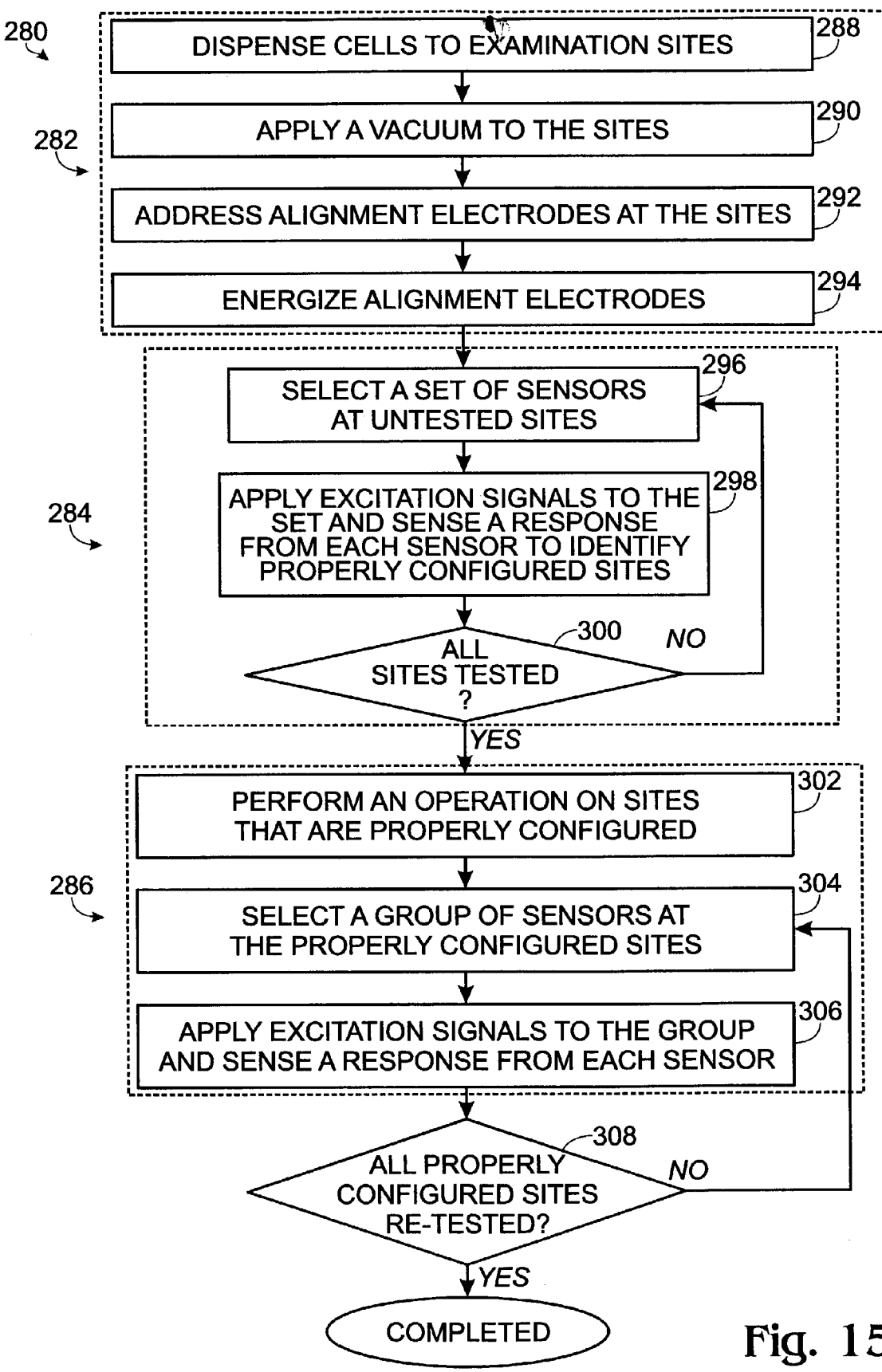
FIG. 15 is a flowchart of an embodiment of a method for selecting examination sites for further manipulation based on electrical signals measured from the examination sites.

FIG. 15 is a flowchart of an embodiment of a method 280 for selecting examination sites for performing additional operations and/or testing based on an electrical property measured at each examination site. Method 280 may be used, for example, to selectively manipulate examination sites having cells or membranes properly positioned (or not properly positioned) at the apertures of the sites. Properly positioned cells or membranes may seal the apertures and thus more effectively impede current flow at the apertures compared to apertures that are not sealed. Accordingly, current flow or another suitable electrical property between outer and inner electrodes may be compared with a threshold value. This comparison may determine whether or not additional operations should be performed at an examination site and/or what additional operations should be performed.

Method 280 may include at least three segments. In one segment, indicated at 282, a series of operations may be conducted to dispose cells or membranes at apertures of examinations sites. In a next segment, indicated at 284, a series of operations may be performed to measure an electrical property of each examination site. These operations may identify examination sites for further manipulation based on the measured electrical property. In a further segment, indicated at 286, additional operations may be conducted on the examination sites identified in preceding segment 284.

Cells or membranes may be disposed at apertures by any suitable procedures. Cells may be dispensed to examination sites, as shown at 288. Generally, cells are dispensed to a receiving or outer compartment at each examination site. Such dispensing may be conducted in fluid, such as a culture medium or a buffer, using, for example, a fluid delivery device such as a pipet or by other fluid flow techniques. A vacuum may be applied to each examination site, as shown at 290. The vacuum may be applied to an inner compartment that opposes the receiving compartment across the aperture at each examination site, to create a negative pressure at the aperture of each site. In some embodiments, the inner compartments are fluidly connected so that the vacuum may be applied at one position to affect many or all of the apertures.

Before, during, and/or after application of the vacuum, alignment electrodes of the examination sites may be addressed or selected, as shown at 292, and energized, as shown at 294. Selection of the alignment electrodes may be conducted, for example, by applying electrical signals to any suitable address selector circuitry. Such electrical signals may create conductive paths from signal elements of the biochip electrical interface to alignment electrodes of the examination sites. Each examination site may include an alignment electrode and a partner electrode, which may flank at least a portion of each aperture. The alignment electrodes may be configured to urge cells within the receiving compartments toward the apertures. In some embodiments, alignment electrodes of all examination sites may be selected at once. Energizing the alignment electrodes may include applying a potential to connected signal elements, for example, a potential supplied by a control apparatus. Such energization may create alignment fields between the alignment electrodes and their partner electrodes, which may electrically polarize cells and urge them toward the apertures. Ultrasonic devices also may be selected and energized before, during, and/or after selecting and energizing the alignment electrodes.

Segment 284 may be used next to measure an electrical property of each examination site. A set of electrical sensors disposed at a corresponding set of untested sites may be selected, as shown at 296. Selection may include energizing address selector circuitry to create conductive paths to appropriate electrical sensors (or sensor electrodes), as described above. In some embodiments, the electrical sensors may be included in different signal groups, enabling efficient use of signal elements at the electrical interface. Next, an electrical excitation signal, such as a voltage may be applied to each sensor of the set, and a response from each sensor may be measured, as shown at 298. This process may test how effectively each aperture at the examination sites is sealed by a cell or membrane. After each set of sites is tested, a determination may be made as to whether all sites have been tested, as shown at 300. If not, method segment 284 may be repeated on another set of untested sites, for example, a different examination site from each signal group, until all sites have been tested. Method segment 284 may be used, for example, to identify examination sites that are properly configured with a cell or membrane at their apertures. Such sites may be distinguished based on the response measured from each electrical sensor. For example, such sites should show a substantially greater resistance to current flow than sites that are not configured properly.

Method segment 286 may be performed on sites that are properly configured. This segment may selectively perform one or more additional operations on properly (or improperly) configured sites, as shown at 302. Such additional operations may include further electrical testing alone or after exposure to test agents. For example, chemical or biological test agents may be dispensed selectively to properly configured examination sites. Such selective dispensation may avoid wasting limited or valuable test agents on improperly configured sites that will not provide data on the test agents. Alternatively, or in addition, properly configured examination sites may be exposed to physical test agents. In some embodiments, properly configured sites may not have any added test agent, but may be analyzed additionally. In any case, electrical properties of the properly configured sites then may be measured. A group of sensors at the properly configured sites may be selected, as shown at 304. Next, an excitation signal may be applied to the each sensor of the group and a response may be measured from each sensor, as shown at 306. A determination then may be made as to whether all properly configured sites have been re-tested after addition of the test agent, as shown at 308. If not, steps 304 and 306 may be repeated for other properly configured sites until all properly configured sites have been re-tested. In some embodiments, a sensor from each signal group may be selected and used for sensing a response, to improve the speed and efficiency with which examination sites are analyzed. Furthermore, in some embodiments, the properly configured sites may be re-tested multiples times, for example, after each of several operations is performed on the sites.

In alternative embodiments, additional operations may be performed selectively on improperly configured sites. Exemplary additional operations may include agitation with an ultrasonic transducer, re-energization of the corresponding alignment electrodes, addition of more cells, introduction of fluid into the examination site, and/or additional perforation treatment at the aperture, among others. Such additional operations may be followed by steps 304 and 306 to determine whether the additional operations altered the measured electrical property at the sites.

It is believed that the disclosure set forth above encompasses multiple distinct embodiments. While each of these embodiments has been disclosed in specific form, the specific embodiments thereof as disclosed and illustrated herein are not to be considered in a limiting sense as numerous variations are possible. The subject matter of this disclosure thus includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

What is claimed is:

1. A biochip device for electrical analysis of biological membranes, comprising:
    a substrate assembly defining an array of apertures and also defining fluid compartments, each aperture providing fluid communication between a pair of the fluid compartments disposed on opposing sides of the aperture, the substrate assembly including thin-film devices configured to sense an electrical property of biological membranes that seal the apertures; and
    an electrical interface coupled electrically to the thin-film devices and configured to electrically couple the thin-film devices to a control apparatus, the electrical interface defining a plurality of interface elements, the biochip device including a greater number of the apertures than of the interface elements,
    wherein the thin-film devices include an electrode and an other thin-film device adjacent each aperture, and wherein the other thin-film device is selected from the group consisting of heaters and ultrasonic transducers.

2. The biochip device of claim 1, wherein the apertures are in numerical excess over the interface elements by a ratio of at least about ten to one.

3. A biochip device for electrical analysis of biological membranes, comprising:
    a substrate assembly defining an array of apertures and including thin-film devices configured to sense an electrical property of biological membranes that seal the apertures; and
    an electrical interface coupled electrically to the thin-film devices and configured to electrically couple the thin-film devices to a control apparatus, the electrical interface defining a plurality of interface elements, the biochip device including a greater number of the apertures than of the interface elements,
    wherein the interface elements include separate address elements and signal elements, the address elements being connected to electronic switching devices that are configured to select apertures for which the electrical property is sensed, the signal elements being configured to carry electrical signals corresponding to the sensed electrical property.

4. The biochip device of claim 1, wherein the electrode and the other thin-film device are independently addressable through the electrical interface.

5. The biochip device of claim 1, wherein the substrate assembly includes a substrate and a plurality of thin-film layers disposed on the substrate, the electrode being a member of a pair of electrodes, and wherein each electrode of the pair is defined at least partially by the same thin-film layer.

6. The biochip device of claim 1, wherein the thin-film devices include at least a pair of independently addressable electrodes for each aperture, the pair being an alignment electrode configured to position a cell electrically at the aperture and a sensor electrode configured to sense the electrical property.

7. The biochip device of claim 1, wherein the thin-film devices include an ultrasonic transducer disposed adjacent each aperture, the ultrasonic transducer being configured to agitate a cell that is disposed out of alignment with the aperture.

8. The biochip device of claim 1, further comprising a fluid barrier attached to the substrate assembly, and forming walls of the fluid compartments.

9. The biochip device of claim 8, the fluid compartments including wells.

10. The biochip device of claim 8, wherein the substrate assembly and the fluid barrier define an array of examination sites, the fluid barrier defining partitions that segregate the apertures to different examination sites.

11. A biochip device for electrical analysis of biological membranes, comprising:
- a substrate assembly defining an array of apertures and also defining fluid compartments, each aperture providing fluid communication between a pair of the fluid compartments disposed on opposing sides of the aperture, the substrate assembly including a plurality of thin-film devices adjacent each aperture, the plurality including
  1) a sensor electrode configured to sense an electrical property of a biological membrane sealing the aperture, and
  2) another thin-film device selected from the group consisting of heaters and ultrasonic transducers.

12. The biochip device of claim 11, wherein the fluid compartments include wells, and wherein each aperture has a corresponding well.

13. The biochip device of claim 11, the substrate assembly including a substrate and a plurality of thin-film layers disposed on the substrate, the thin-film layers providing the thin-film devices, the thin-film devices including a partner electrode configured to form an electric field in cooperation with the sensor electrode as the sensor electrode senses, the sensor electrode and the partner electrode each being provided at least partially by the same thin-film layer.

14. The biochip device of claim 11, wherein the biological membrane is provided by a cell, the plurality of thin-film devices including another electrode configured to promote movement of the cell toward the aperture.

15. The biochip device of claim 11, wherein the thin-film devices are addressable independently.

16. The biochip device of claim 11, the other thin-film device being spaced from the aperture.

17. The biochip device of claim 11, further comprising an electrical inter face configured to connect the thin-film devices to a control apparatus, the electrical interface including interface elements, the biochip device including a greater number of the apertures than of the interface elements.

18. The biochip device of claim 11, wherein the substrate assembly includes a substrate and a passivation layer, each aperture being at least partially defined by the passivation layer to restrict fluid in the aperture from contacting the substrate.

* * * * *

UNITED STATES PATENT AND TRADEMARK OFFICE
CERTIFICATE OF CORRECTION

PATENT NO. : 7,112,433 B2
APPLICATION NO. : 10/423166
DATED : September 26, 2006
INVENTOR(S) : David Tyvoll et al.

It is certified that error appears in the above-identified patent and that said Letters Patent is hereby corrected as shown below:

In column 16, line 66, in Claim 8, after "assembly" delete ",".

In column 17, line 1, in Claim 9, delete "blochip" and insert -- biochip --, therefor.

In column 17, line 24, in Claim 13, delete "blochip" and insert -- biochip --, therefor.

In column 18, line 16, in Claim 17, delete "inter face" and insert -- interface --, therefor.

Signed and Sealed this

Fifth Day of May, 2009

JOHN DOLL
*Acting Director of the United States Patent and Trademark Office*